United States Patent [19]
Gordon et al.

[11] Patent Number: 4,902,476
[45] Date of Patent: Feb. 20, 1990

[54] HEAT EXCHANGER AND BLOOD OXYGENATOR APPARATUS

[75] Inventors: Lucas S. Gordon, Laguna Beach; Richard L. Bringham, San Clemente, both of Calif.

[73] Assignee: Baxter International Inc., Deerfield, Ill.

[21] Appl. No.: 56,135

[22] Filed: May 29, 1987

Related U.S. Application Data

[63] Continuation-in-part of Ser. No. 767,060, Aug. 19, 1985, abandoned, which is a continuation of Ser. No. 457,875, Jan. 14, 1983, abandoned.

[51] Int. Cl.$^4$ ............................................. A61M 1/14
[52] U.S. Cl. ...................................... 422/46; 422/48; 128/DIG. 3; 261/DIG. 28; 165/161; 165/184
[58] Field of Search ...................................... 422/45–48; 165/184, 161; 210/321.8; 128/DIG. 3; 261/DIG. 28

[56] References Cited

U.S. PATENT DOCUMENTS

| | | |
|---|---|---|
| 2,146,141 | 12/1936 | Harris . |
| 2,399,484 | 12/1943 | Gunter . |
| 4,138,288 | 2/1979 | Lewin . |
| 4,138,464 | 2/1979 | Lewin . |
| 4,424,190 | 1/1984 | Mather, III et al. ............. 422/48 X |
| 4,428,934 | 1/1984 | Raible . |
| 4,559,999 | 12/1985 | Servas et al. ..................... 422/46 X |
| 4,653,577 | 3/1987 | Noda ................................. 422/46 X |

Primary Examiner—Barry S. Richman
Assistant Examiner—Lynn M. Kummert
Attorney, Agent, or Firm—Michael C. Schiffer; Gordon I. Peterson

[57] ABSTRACT

A heat exchanger and blood oxgenator apparatus includes a housing having a blood inlet portion, a blood outlet portion, and a housing wall defining an enclosed chamber disposed along a chamber axis between the blood input portion and the blood output portion through which to pass a quantity of blood to be temperature controlled. A heat exchanger tube having an exterior surface and a hollow interior through which to pass a heat exchange medium for purposes of exchanging heat with a quantity of blood brought into contact with the exterior surface, is disposed in a generally helical coil that is mounted within the chamber to encircle the chamber axis. A scalloped inner surface is included on the housing wall to face generally inward toward the heat exchanger tube. Spacing members disposed between the exterior surface of the heat exchanger tube and the scalloped inner surface of the housing wall retain the exterior surface spaced apart from the scalloped inner surface to define a flow passage through which to pass a quantity of blood so that the blood contacts a substantial portion of the exterior surface.

4 Claims, 7 Drawing Sheets

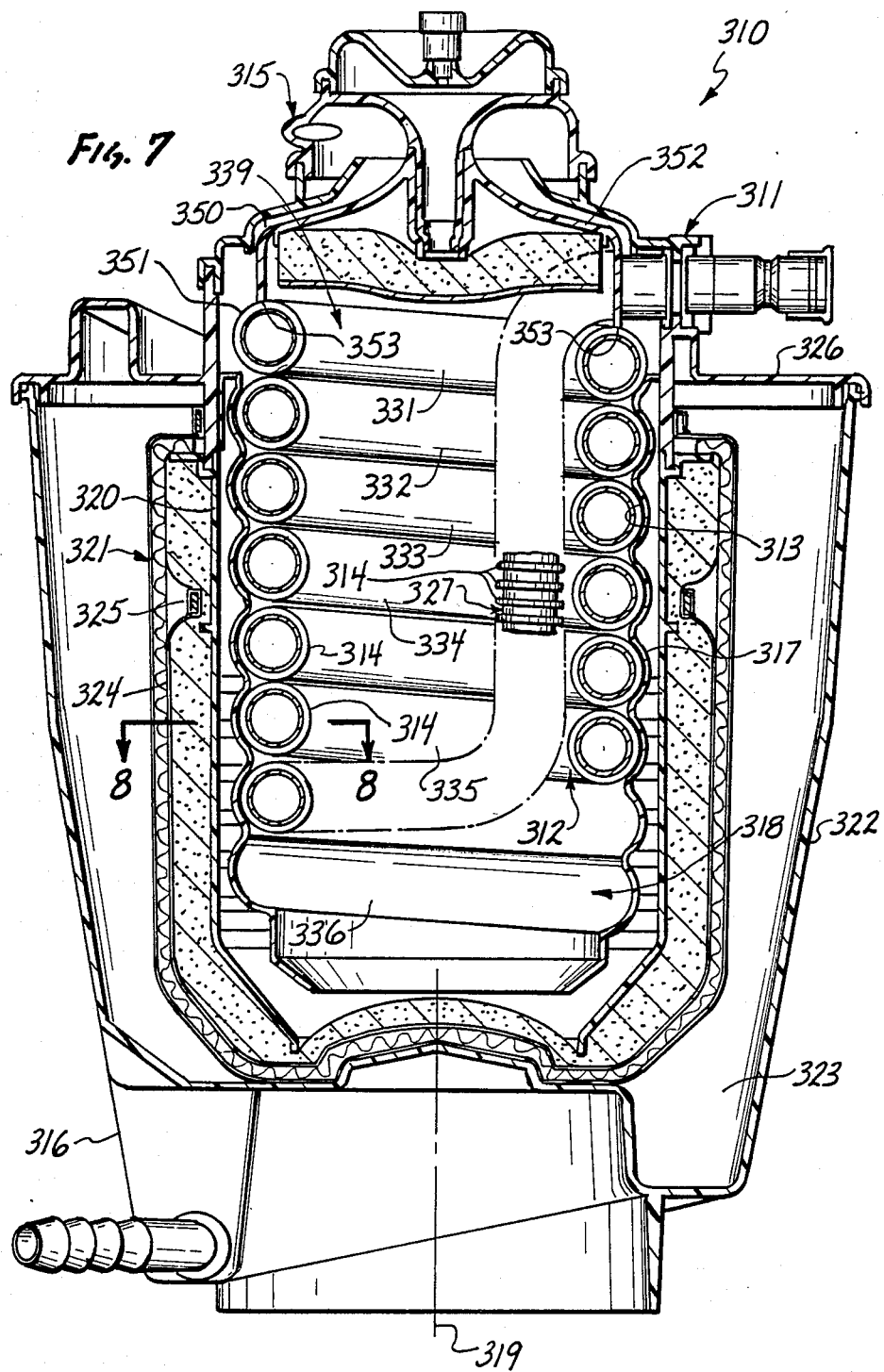

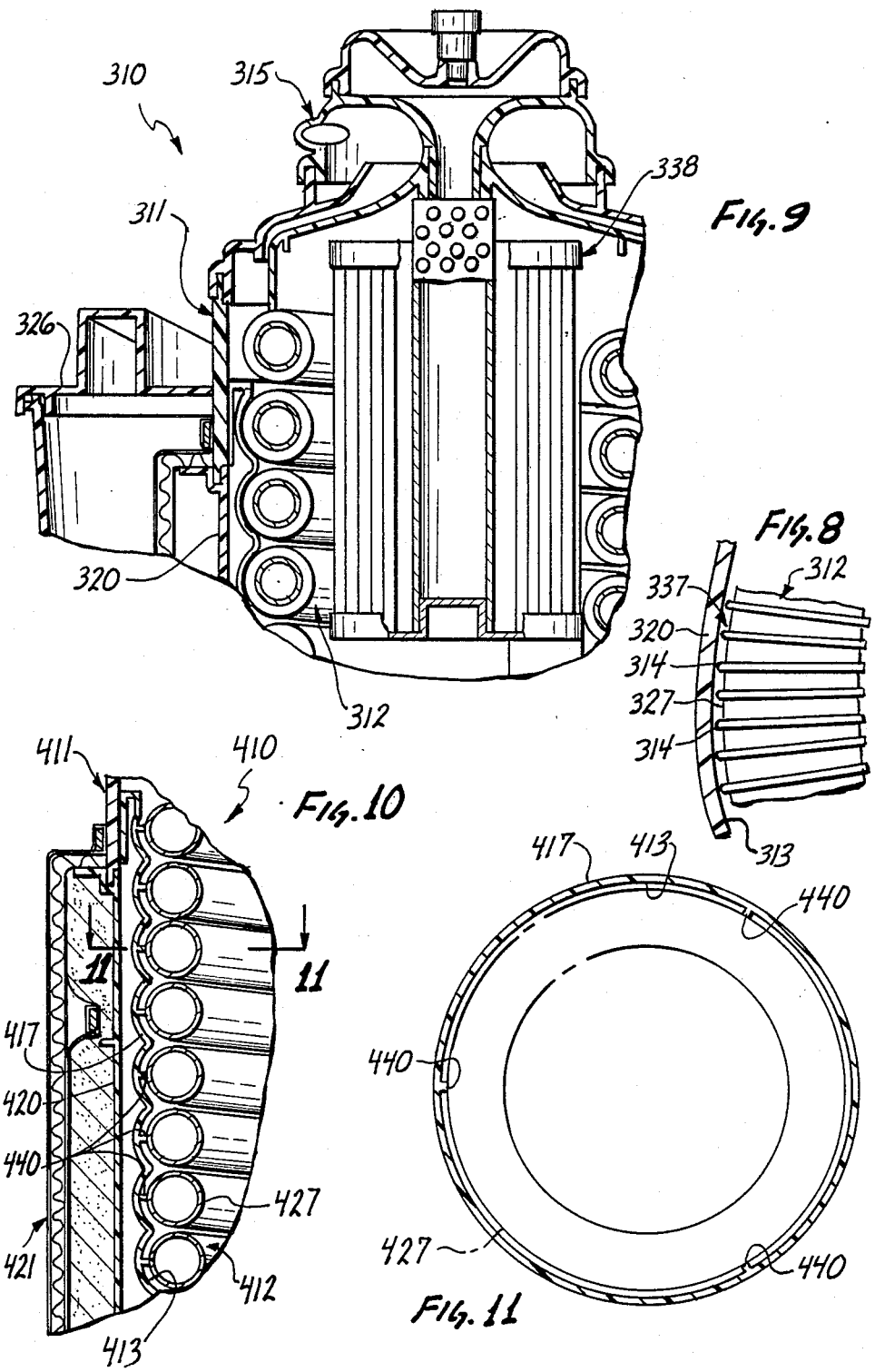

HEAT EXCHANGER AND BLOOD OXYGENATOR APPARATUS

CROSS REFERENCE TO RELATED APPLICATIONS

This application is a continuation-in-part of copending U.S. patent application Ser. No. 767,060, filed Aug. 19, 1985, which is a continuation of U.S. patent application Ser. No. 457,875, filed Jan. 14, 1983, both now abandoned.

BACKGROUND OF THE INVENTION

1. Technical Field

The invention relates generally to the control of blood temperature during various operative procedures in which blood is introduced into a patient, and more particularly to a new and improved heat exchanger apparatus for this purpose.

2. Background Information

Blood temperature must be carefully controlled prior to introduction into a patient according to the operative procedure undertaken. In this regard, the blood may be heated to a desired temperature as high as thirty-seven degrees Centigrade, and it may be cooled to as low as five degrees Centigrade for some infant surgery. Heat is either added or withdrawn from the blood to accomplish this, and a heat exchanger performs this function.

The novel blood oxygenator heat exchanger described in the above-identified related applications is adapted to be inserted in an extracorporeal loop for this purpose. Blood from the patient passes through the apparatus and then back to the patient. As it flows through the apparatus it is oxygenated and brought to the desired temperature.

This is done with a heat exchanger tube wound into a helical coil through which a heat transfer fluid, such as water, is passed. The tube is disposed between two surfaces and employs a bellows configuration, i.e., a plurality of individual external ribs on the heat exchanger tube, that result in the tube having reduced cross-sectional area regions between the ribs. Each of the inner and outer surfaces is scalloped to define generally vertical passages along the reduced cross-sectional area regions between adjacent windings of the coil. Blood flows from an oxygenator arrangement along a generally vertical, gently undulating blood flow path through the reduced cross-sectional area regions, and this results in the exchange of heat between the blood and the heat transfer fluid.

There are some aspects that could be further refined, however. For example, a heat exchanger apparatus with less complicated, and correspondingly less costly, structure is desirable. Also, it is sometimes desirable to employ a cardiotomy filter in operative procedures in which the heat exchanger is used. Thus, it would be desirable to have an apparatus adapted to receive such a filter, in order to have a compact, multifunction, blood processing station.

In addition, it is sometimes desirable to bring blood to a desired temperature apart from oxygenating or otherwise processing the blood. Preheating donor blood for rapid blood infusion provides an example. Thus, it is desirable to have a stand alone heat exchanger apparatus that can be used for this limited purpose.

SUMMARY OF THE INVENTION

This invention recognizes the problems associated with the prior art and provides a new and improved heat exchanger apparatus with the desired attributes.

Briefly, the above and further objects of the present invention are realized by providing an apparatus that employs a hellically-coiled heat exchanger tube mounted within a housing to define a flow passage between the tube and a scalloped surface on the housing. The flow passage provides an undulating flow pattern in which the blood contacts a substantial portion of the exterior surface of the heat exchanger tube. Thus, effective heat exchange is accomplished with little blood agitation. In addition, one embodiment is gravity fed and includes space for a separate filter element.

Generally, the apparatus includes a housing having a blood inlet portion, a blood outlet portion, and a housing wall defining an enclosed chamber disposed along a chamber axis between the input portion and the output portion through which to pass a quantity of blood to be temperature controlled. A heat exchanger tube is included that has an exterior surface and a hollow interior through which to pass a heat exchange medium for purposes of exchanging heat with a quantity of blood brought into contact with the exterior surface. The heat exchanger tube is disposed in a generally helical coil that is mounted within the chamber to encircle the chamber axis.

According to one aspect of the invention, there is provided a scalloped inner surface on the housing wall that faces generally inward toward the heat exchanger tube. Spacing members are disposed between the exterior surface of the heat exchanger tube and the scalloped inner surface of the housing wall for retaining the exterior surface spaced apart from the scalloped inner surface. This functions to define a flow passage through which to pass a quantity of blood so that the blood contacts a substantial portion of the exterior surface.

According to another aspect of the invention, there is provided spacing members in the form of either or both of a plurality of spaced-apart, circumferentially-extending ribs on the heat exchanger tube and a plurality of protrusions on the housing wall. According to yet another aspect of the invention, there is provided an input passage that conveys blood evenly to a central portion of an uppermost winding of the heat exchanger tube. Still another aspect provides a space encircled by the heat exchanger tube that is adapted to receive a separate filter element.

The above mentioned and other objects and features of the invention and the manner of attaining them will become apparent, and the invention itself will be best understood, by reference to the following description taken in conjunction with the accompanying illustrative drawings.

BRIEF DESCRIPTION OF THE DRAWINGS

FIG. 7 is an elevational view taken in cross section of a first of two heat exchanger apparatuses embodying the invention;

FIG. 8 is an enlarged cross section of a portion of the first heat exchanger taken on line 8—8 of FIG. 7 that further illustrates the abutting relationship of the heat exchanger tube;

FIG. 9 shows a cross section of a portion of the first heat exchanger apparatus with a cardiotomy filter installed;

FIG. 10 shows a portion of a second heat exchanger apparatus similar to in many respects to the first apparatus, but which employs spacing members in the form of protrusions on the housing wall; and FIG. 11 is a cross sectional view of the second heat exchanger apparatus taken on line 11—11 of FIG. 10.

DESCRIPTION OF THE PREFERRED EMBODIMENTS

Figure 1:
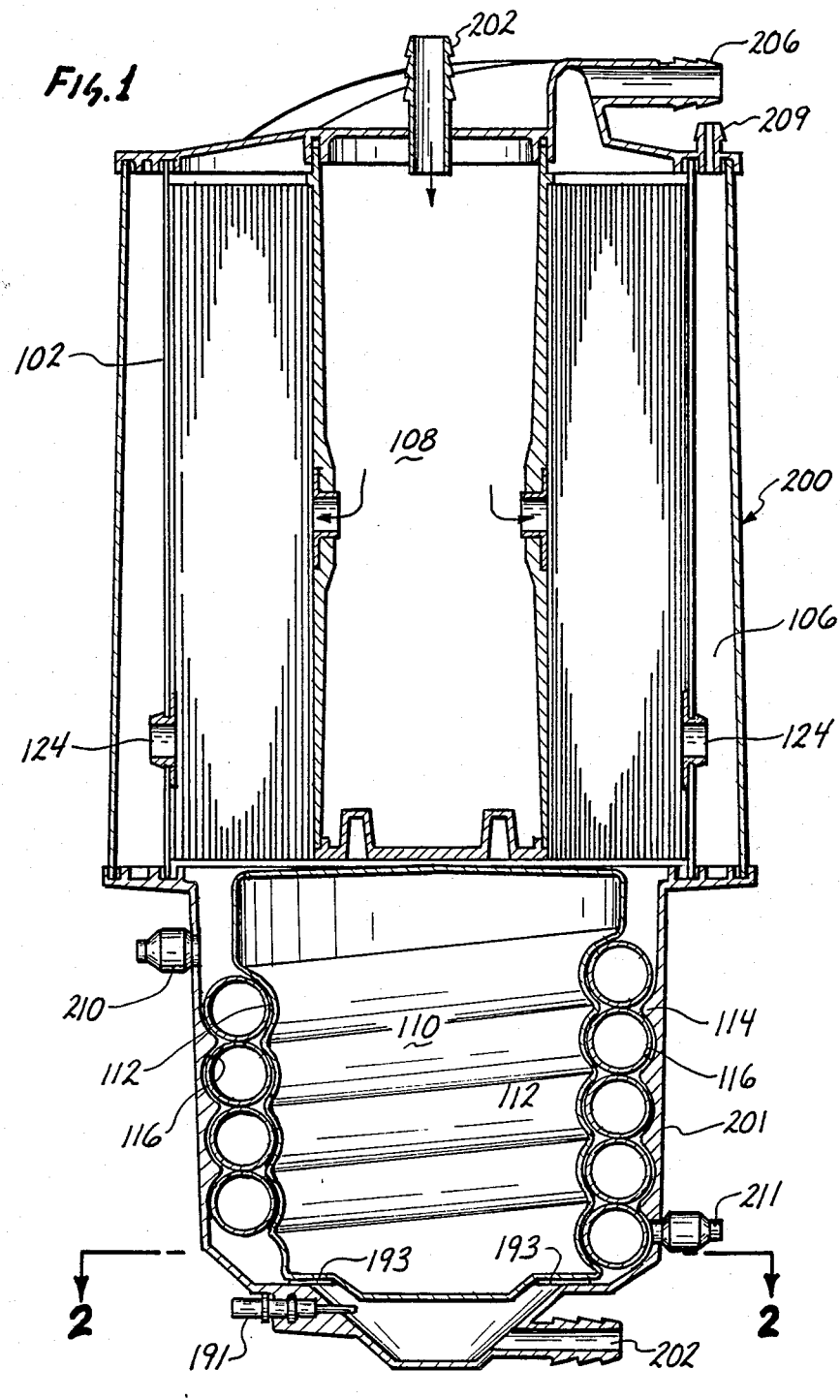
FIG. 1 is a cross-sectional view of a blood oxygenator heat exchanger constructed according to the invention.

The invention is described in further detail with reference to the drawings by (1) an introduction, (2) a description of the three embodiments of the blood oxygenator heat exchanger that is substantially as originally disclosed in the above-identified related applications, and (3) a detailed description of two heat exchanger apparatuses embodying the invention.

INTRODUCTION

The history of safe and reliable blood oxygenators is relatively brief. Such oxygenators are used in open-heart surgery and other operations and treatments of the body when it is necessary to establish an extracorporeal circulation system for temporarily assuming the functions of the heart and lungs of the patient.

In such a system, the oxygenator operates to perform the function usually performed by the lungs of the patient, i.e., the life-supporting transfer of oxygen into the blood and transfer carbon dioxide out of the blood. The oxygenator is used in association with a pump which performs the function of the heart to cause circulation of the blood. Thus, early versions of the oxygenator were often referred to as "heart-lung" machines.

The early heart-lung machines were typically rotating discs which passed through a pool of blood, but were only partially immersed therein such that the free surface of the disc exposed the blood to oxygen and accomplished some gas transfer. After this, bag-type oxygenators were introduced which were superior to the disc oxygenators, but which left much to be desired.

A major advance occurred in the mid-1960's when the rigid (or hard shell) bubble oxygenator was developed. The history of such oxygenators had its beginnings in the device shown in Raible, et al., U.S. Pat. No. 3,468,631, which is incorporated herein by reference, and they first came into clinical use with the development of the devices shown in Bentley et al., U.S. Pat. Nos. 3,488,158 and 3,578,411 which have come to be known as the Bentley oxygenator. At the present time, such oxygenators are used more frequently than any other type. Among the important features of the oxygenators disclosed in the foregoing patents was the provision of a self-contained heat exchanger.

In the intervening years, some relatively minor modifications have been made in bubble oxygenators, e.g., those disclosed in Brumfield U.S. Pat. Nos. 3,764,271 and 3,769,162. Bentley, et al. U.S. Pat. Nos. 3,488,158 and 3,578,411 and the Brumfield patents have some downward portions in the flow path of the gas blood mixture, but it is clear that they were designed to provide for initial upward flow of the gas and blood mixture in that portion of the flow path where the bubbles are formed.

In addition, Fields U.S. Pat. No. 3,204,631, discloses an oxygenator in which blood enters at an upper portion and oxygen enters at a lower portion such that there is a counterflow relationship with the blood initially flowing downwardly and the oxygen flowing upwardly. Further Lewin U.S. Pat. No. 4,138,464 shows the desirability of alternate positioning of fluid connections for an oxygenator device.

The blood oxygenator heat exchanger subsequently described is a further improvement of the device shown in the Bentley U.S. Pat. No. 3,165,238, issued Oct. 26, 1971, entitled "Oxygenator"; the Bentley, et al., U.S. Pat. No. 3,578,411 issued May 11, 1971, entitled "Bubbler Assembly for Blood Treating Apparatus"; the Bentley, et al., U.S. Pat. No. 3,488,158, issued Jan. 6, 1970, entitled "Bubbler Assembly for Oxygenator"; and application, Ser. No. 436,913, entitled "Blood Oxygenator", now abandoned, Ser. No. 565,043, now U.S. Pat. No. 4,058,369, entitled "An Improved Oxygenator" that issued as U.S. Pat. No. 4,297,318 the disclosures of which are incorporated by reference herein. These devices each represent important developments in the blood treatment art. However, since these devices temporarily assume the initial function of the heart and lungs of a patient during certain operations or other treatments of the body, further improvements are desired.

Other oxygenator configurations allow for the oxygen transfer to be accomplished across a gas permeable membrane formed either in a continuous sheet or a plurality of hollow fibers. The heat exchanger coil of the blood oxygenator heat exchanger subsequently described may be employed in conjunction with these membrane or hollow fiber oxygenators as well as hard shell bubble oxygenators.

A significant advance in the area of blood oxygenators self-contained heat exchangers occurred in the early 1960's with the development of the blood oxygenators integral heat exchanger developed by Richard DeWall, U.S. Pat. Re. No. 27,100, also assigned to the assignee of this invention, Bentley Laboratories. Other significant work was performed by Dr. Frank Gollan, see pages 69–72 of *Heart-Lung Bypass, Principles and Techniques of Extracorporeal Circulation* (1962), Pierre Galletti, M.D. Ph.D. et al. In the following years relatively minor modifications to the work of Dr. Gollan were made, e.g., those disclosed by Lewin U.S. Pat. Nos. 4,065,264, 4,138,464 and 4,138,288, as to these three Lewin patents, see specifically FIG. 15 of U.S. Pat. No. 4,138,288 where an "annular ribbed" heat exchanger is shown.

BLOOD OXYGENATOR HEAT EXCHANGER

Considering now FIGS. 1–6, there are shown three embodiments of the blood oxygenator heat exchanger of the invention. Briefly, the blood oxygenator heat exchanger contains means for combining oxygen-containing gas with liquid blood and a self contained heat exchanger coil. The heat exchanger coil has a bellows configuration including a number of individual smooth rounded surface ribs each spaced apart from the next by a smaller diameter coil section. Preferably inner and outer scalloped members engage opposed portions of the bellows ribs to assist in providing a generally vertical, gently undulating blood flow path, primarily through the coil smaller diameter sections, along adjacent windings of the heat exchanger coil.

The bellows coil is configured with certain critical tolerances such that the axial length of the smaller diameter coil sections effect a reduced blood priming volume and a low pressure resistive blood flow path between the adjacent bellows ribs while at the same time allowing for as many bellows ribs as possible per unit length. This axial length of the smaller diameter coil section should allow for proper application of a biologically compatible coating to the exterior of the coil.

Additionally, the axial length of the bellows rib, preferably hollow, should be sufficient to allow adequate heat transfer fluid flow but also to allow for as many bellows ribs per unit length as possible. The internal diameter of the bellows coil must be of sufficient size as to reduce the heat transfer fluid (typically water) pressure drop through the coil. The internal diameter of the smaller diameter section should be maximized in order to reduce vibration of the heat exchanger coil.

The ratio of the outer diameter of the heat exchanger ribs to the outer diameter of the smaller diameter sections is between about one and two-tenths and about two. The axial length of the heat exchanger small diameter section is between about three hundredths and about eighteen hundredths of an inch. The axial length of each of the heat exchanger ribs is between about two hundredths and twenty hundredths of an inch. The ratio of the axial length of the heat exchanger smaller diameter sections to the axial length of the heat exchanger ribs is between about one-tenth and about nine. Further, the ratio of the heat exchanger coil internal diameter to the outer diameter of the heat exchanger ribs is between about four tenths and about eight tenths.

Figure 4:
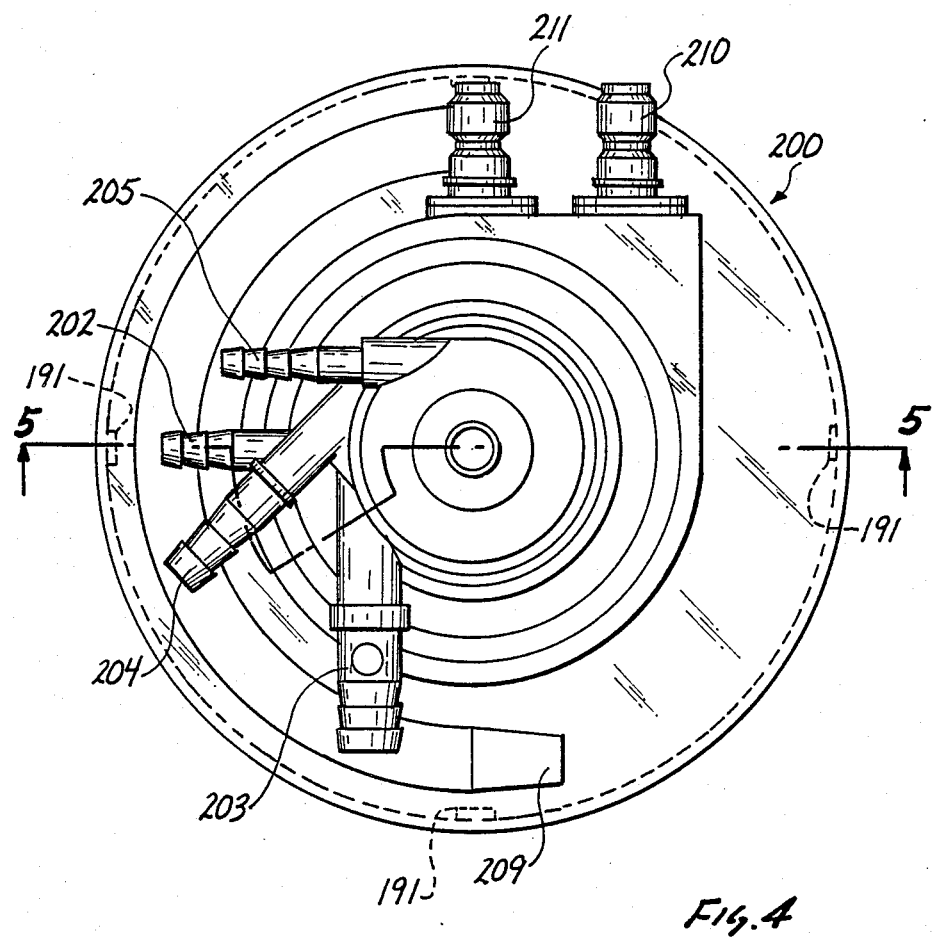
FIG. 4 is a top view of a second embodiment of the blood oxygenator heat exchanger.
Figure 5:
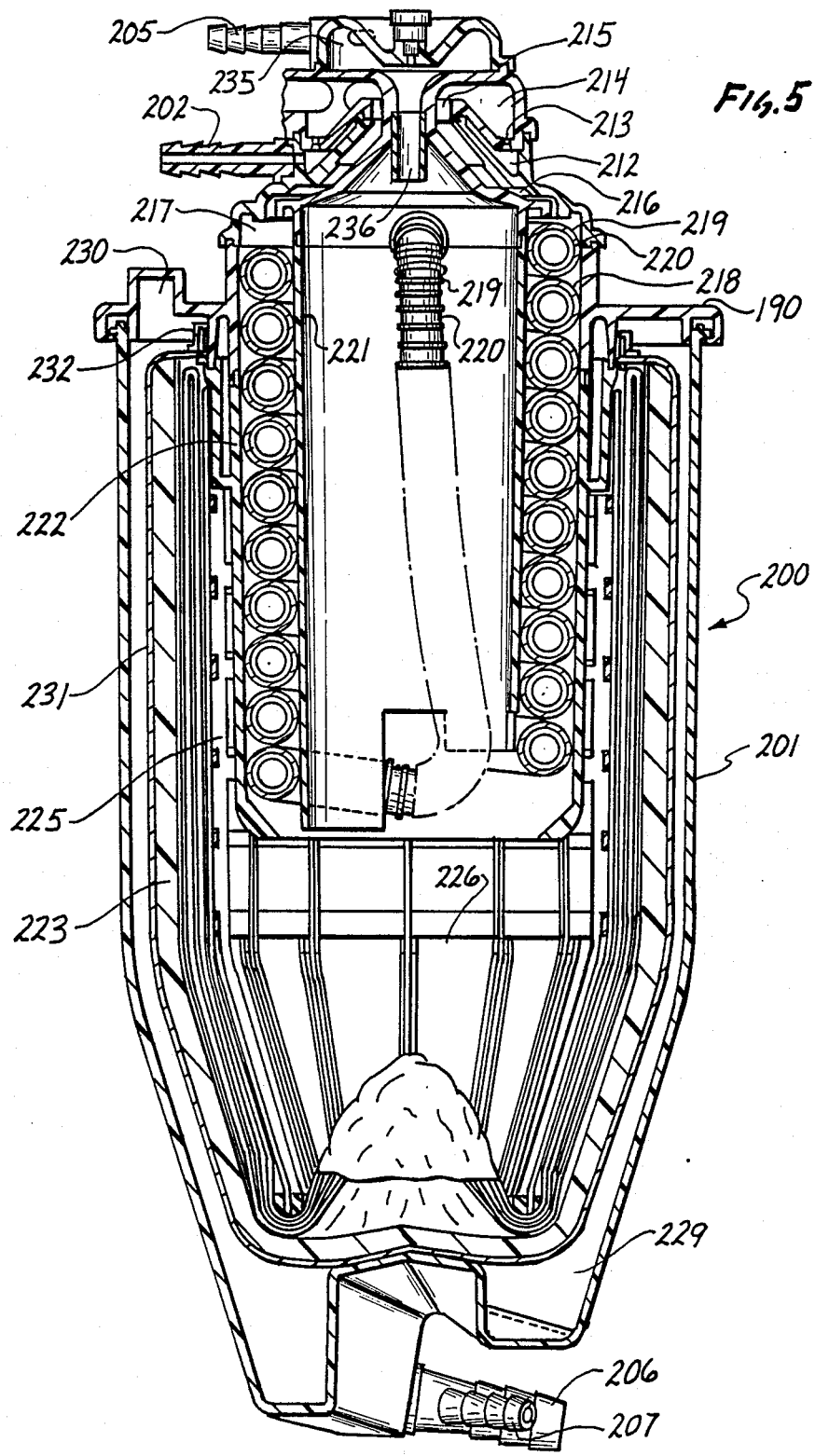
FIG. 5 is a cross-sectional view taken on line 5—5 of FIG. 4.

Referring to FIGS. 4 and 5, there is shown an oxygenator 200 that includes an oxygen-containing gas inlet 202 and a pair of blood inlets 203 and 204. An inlet 205 is provided for priming as well as for optimal medical administration and, if needed, as a return inlet from the cardiotomy reservoir.

A gas vent 209 is provided as are an inlet 210 and an outlet 211 for heat exchanger fluid. The gas inlet 202, the blood inlets 203 and 204, the inlet 205, the vent 209 and the heat exchanger fluid inlet 210 and outlet 211 are preferably located in a cap portion 190, as shown in FIG. 5. The cap portion 190 of the blood oxygenator 200 is rotatably connected to an outer shell portion 201 of the oxygenator 200. Preferably, the outer shell portion 201 of the blood oxygenator includes a pair of blood outlets 206 and 207.

Referring now to FIG. 5, the internal construction of the oxygenator 200 is shown in greater detail. As there depicted, the gas inlet 202 connects with an annular chamber 212 which is bounded on its upper end by a diffusion means 213. The diffusion means 213 may be a perforated member.

The blood inlet means 203 and 204 connect with the interior of an annular chamber 214 in a generally tangential manner. Thus, when the chamber 214 is filled with blood, flowing in a spiral manner, the oxygen-containing gas is admitted to the device through the inlets 202. This gas, such as oxygen or an oxygen-rich mixture, passes through the inlet 202 into the chamber 212 and through the diffusion means 213 into the body of the blood in the chamber 214.

The chamber 214 connects with an annular chamber 215 and an undulating distribution channel 216, the latter being conical in general shape. The channel 216 connects with an annular mixing chamber 217 which is provided with a heat exchange tube 218 and which contains a descending flow path for the blood. The heat exchanger-tubing 218 is a bellows tubing having large diameter individual ribs portion 219 and a small diameter section 220. There are a plurality of descending flow paths between the walls of the mixing chamber 217 and the wall of the tubing 218 formed by the convolutions.

At the lower end of the chamber 217, an outer wall 222 terminates approximately two-thirds of the distance from the top to the bottom of the oxygenator to permit bubbles of blood to come into contact with a defoaming means 223. Thus, the elevation of the blood outlets 206 and 207 is lower than the bottom of the tortuous flow path in the mixing chamber 217. While several defoaming means may be used, e.g., that disclosed in U.S. Pat. No. 3,468,631, it is preferred to form the foaming material from a polyurethane foam having approximately ten to thirty pores per inch. The polyurethane foam is coated with a silicone defoaming agent. Optimally, a spacer 225 may be provided between the defoaming material 223 and the wall 222. The spacer 225 may comprise a rib structure which provides open spaces therebetween.

A plurality of open spaces 226 are provided in spacer 225 which permits blood to come into contact with a defoaming material reservoir 229 where liquid blood is collected.

An annular passage 230 connects with the vent means 209 so that vent gases may be exhausted from the oxygenator. A mesh sleeve 231 which may be polyester, polypropylene, polyethylene, nylon or other suitable fabric is positioned about the defoaming material 223 and is provided with an elastic strap 232 to hold it in place. A port 205 connects with a chamber 235 which, in turn, connects with a conduit 236. The port 205 is used for priming the oxygenator and may also be used for addition of medication to the blood or for blood coming from the cardiotomy reservoir.

Figure 2:
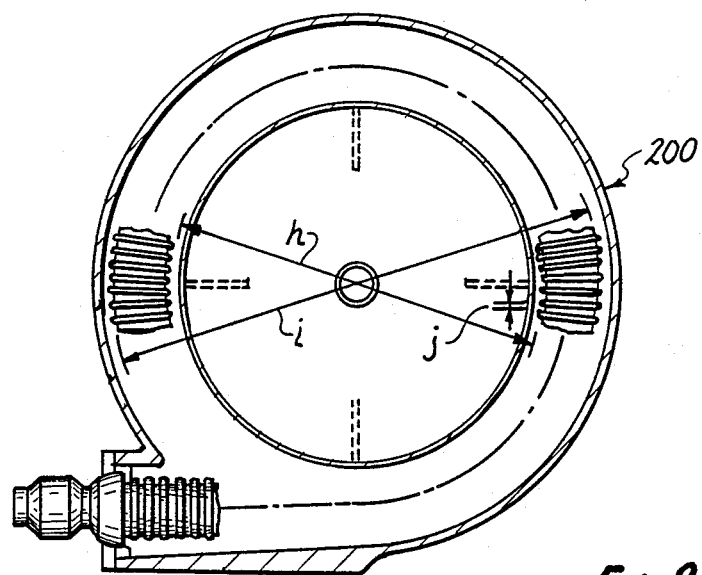
FIG. 2 is a cross sectional view taken on line 2—2 of FIG. 1.
Figure 6:
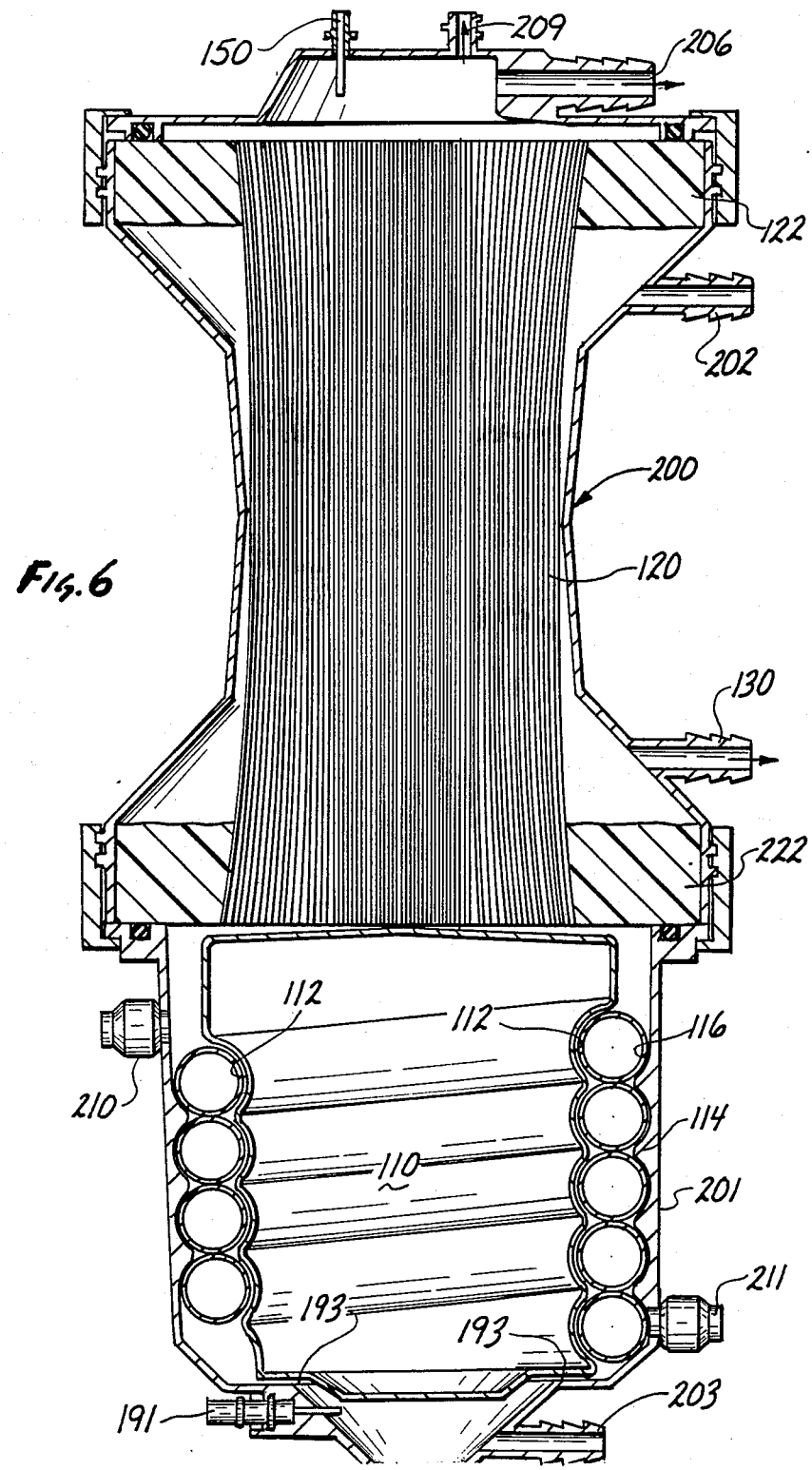
FIG. 6 is a cross-sectional view of a third embodiment of the blood oxygenator heat exchanger.

Alternate oxygenator embodiments include a membrane oxygenator shown in FIGS. 1 and 2 and a hollow fiber oxygenator as shown in FIG. 6. Referring first to FIG. 1, the illustrated oxygenator 200 includes a blood inlet 203. A probe 191 allows for temperature measurement of the mixture of oxygen and blood. A blood outlet 206 is provided as is an inlet 210 and an outlet 211 for heat transfer fluid. An oxygen-containing gas inlet 202 conveys oxygen into a hollow central chamber 108 from which it passes into the interior of a hollow membrane tube 102 which is wrapped lengthwise about a central chamber 108. The gas exits the wrapped membrane at outlets 124 into an annular exit chamber 106 and is vented through a gas vent 209.

An insert 110 provides an inner scalloped member having individual scallop surfaces 112 which engage opposed portions of the heat exchange ribs 219. An outer scalloped member 114 is provided by the inner portion of outer shell 201 and has individual scallop surfaces 116 which also engage opposed portions of the heat exchanger ribs 219. Because the heat exchanger coil 218 is helically wrapped within oxygenator 200, insert 110 may be threaded into the coil into the orientation shown in FIGS. 1 and 6. Spacers 193 provide a stop for the insert 110 and provide a blood passage into the area of the helically wrapped coil 218. Blood leaves the heat exchange coil 218 and then passes along the exterior of the wrapped membrane 102 and then out through blood outlet 206.

Figure 3:
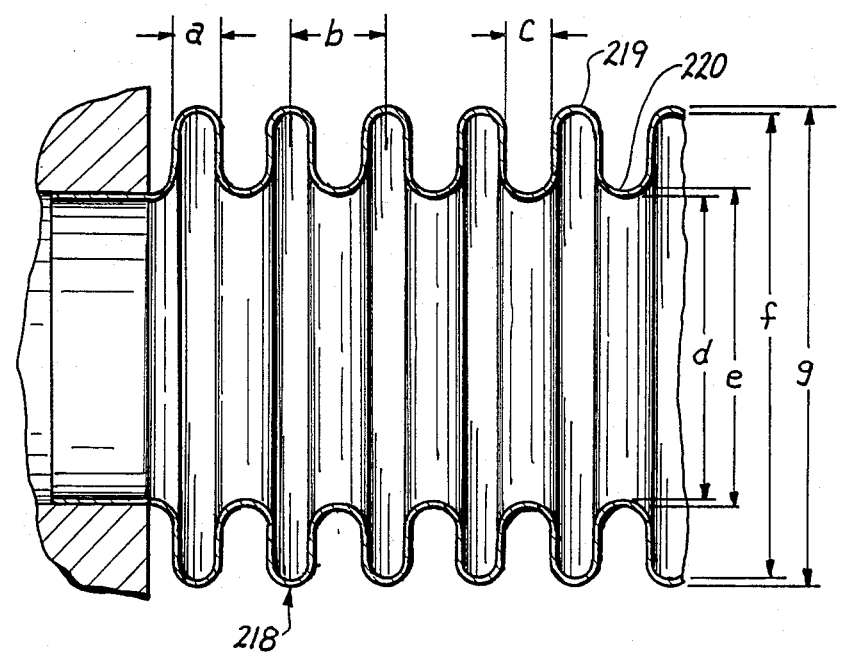
FIG. 3 is a partial cross-sectional view of the heat exchanger tube of the blood oxygenator heat exchanger.

Referring now to FIG. 3, "a" refers to the axial length of each of the heat exchanger ribs 219 while "c" represents the axial length of the heat exchanger smaller diameter sections 220. Reference "b" refers to the center spacing of adjacent ribs 219. Reference "d" represents the heat exohanger coil 220 and heat exchanger smaller diameter sections 220 internal diameters while "e" represents the outside diameter of the heat exchanger smaller diameter sections 220. Reference letters "f" and "g" refer to the internal and external diameters of the heat exchanger ribs 219, respectively.

FIG. 2 shows the heat exchanger coil internal and external diameters "h" and "i", respectively. Also shown in FIG. 2 is "j" which represents the spacing between adjacent ribs when the heat exchanger 220 is coiled as shown in FIG. 2. Spacing "j" is preferably more than twenty percent (20%) of the axial length of the heat exchanger smaller diameter sections "b".

Referring now to FIG. 6, a blood oxygenator is shown having a heat exchanger section similar to that illustrated in FIG. 1. The oxygenator section differs in that oxygenation is accomplished through use of a plurality of hollow fibers 120 embedded at each end within an urethane material, or the like, 122. Blood having passed upwardly through the inside of hollow fibers 120 exits the blood oxygenator 200 through blood outlet 206. A gas vent 130 allows for the venting of gas. An oxygen-containing gas inlet 202 and a gas outlet 130 are provided for circulating gas around the exterior of the hollow fibers 120. FIG. 6 shows temperature probe 150 at the blood outlet region as well as probe 191 for temperature measurement at the region of the blood inlet and arterial blood sample port 209.

Thus, a blood oxygenator heat exchanger embodying the invention includes a housing (which may include, for example, outer shell 201) having a blood inlet, a blood outlet, and a housing wall (such as the outer shell 201). This defines an enclosed chamber disposed along a chamber axis (extending generally up the center of the outer shell 201) between the blood inlet and the blood outlet through which to pass a quantity of blood to be temperature controlled.

In addition, the blood oxygenator includes a heat exchanger tube (tube 218) having an exterior surface (small diameter section 220 of tube 218) and a hollow interior through which to pass a heat exchange medium for purposes of exchanging heat with a quantity of blood brought into contact with the exterior surface. The heat exchanger tube is disposed in a generally helical coil that is mounted within the chamber to encircle the chamber axis.

A scalloped inner surface on the housing wall (individual scalloped surfaces 116) faces generally inward toward the heat exchanger tube, and spacing members (individual ribs portion 219 of the tube 218) are provided between the exterior surface of the heat exchanger tube and the scalloped inner surface of the housing wall for retaining the exterior surface spaced apart from the scalloped inner surface. This results in a flow passage between the exterior surface of the heat exchanger tube and the scalloped inner surface of the housing wall through which to pass a quantity of blood so that the blood contacts a substantial portion of the exterior surface.

Although two scalloped members are illustrated, only one need be employed within the inventive concepts described. Although a small amount of blood may follow a generally helical path along the coil parallel to the convolutions of the heat exchanger coil in the spaces between adjacent windings of the coil, the vast majority of the blood follows a scalloped, generally vertical path in the vertically extending recesses defined by surfaces 112 and 116, even if only one scalloped member is employed. The scalloped vertical flow of the blood allowed by the structure of FIGS. 1-3, produces a laminar blood flow transverse to the heat exchanger coils that is highly effective for heat exchange, yet is short enough to minimize the risk of hemolysis and thrombus formation.

Each one of the individual ribs portion 219 generally abuts the scalloped inner surface of the housing wall to retain the exterior surface of the heat exchanger tube spaced apart from the scalloped inner surface in order to define the vertically disposed flow passage. This, and other aspects of the invention will be subsequently described more fully with reference to two heat exchanger apparatuses embodying the invention.

HEAT EXCHANGER

Referring now to FIGS. 7-10, there are shown two heat exchanger apparatuses 310 and 410 constructed according to the invention. Considering first the apparatus 310 in FIG. 7, it includes many features of the blood oxygenator heat exchangers illustrated in FIGS. 1-6, along with other inventive attributes subsequently described.

Generally, the apparatus 310 includes a housing 311, a heat exchanger tube 312 disposed in a generally helical coil that is mounted within the housing 311, and a scalloped inner surface 313 that faces generally inward toward the heat exchanger tube 312. Spacing members 314 are disposed between the heat exchanger tube 312 and the scalloped inner surface 313 to define a flow passage through which to pass a quantity of blood. So configured, blood passing through the flow passage contacts a substantial portion of the heat exchanger tube 312 for effective heat exchange.

Considering first the housing 311, it includes a blood inlet portion 315 through which to introduce a quantity of blood into the housing 311, and a blood outlet portion 316 through which to discharge the blood. It includes a generally cylindrical tubular member or housing wall 317 that defines an enclosed chamber 318 in which the heat exchanger tube 312 is mounted. The scalloped inner surface 313 is a part of the housing wall 317, and the chamber 318 defined by the housing wall 317 extends between the blood inlet portion 315 and the blood outlet portion 316 along a generally vertical chamber axis 319.

An apertured cage 320 circumscribes the housing wall 317 in spaced apart relation to the housing wall 317, to function as a support structure for a defoaming member or sock 321 composed of one or more layers of porous material through which the blood passes as it flows to the blood outlet portion 316. This serves what is commonly called a defoaming function to further process the blood before introduction into a patient.

An outer housing 322 circumscribes the sock 321 to define an enclosed well or reservoir 323 in which blood collects before passing through the blood outlet portion 316. The illustrated apparatus 310 includes a microscreen 324 as one layer of the sock 321 to reduce the flow of microbubbles, and it terminates at a predetermined maximum level 325 to which it is desired that the reservoir 323 fill with blood. Thus, if the microscreen 324 becomes blocked, blood can bypass the microscreen 324 and still flow to the blood outlet portion 316.

As an idea of size, the apparatus 310 is approximately thirty centimeters high, and the outer housing 322 is approximately twenty centimeters in diameter at its widest point. The blood outlet portion 316 may be configured so that it is adapted to be attached atop a blood oxygenator module or other device with which it is to be used, and the housing 311 may include a lid portion 326 for use in removably mounting the housing 311 atop the outer housing 322, in the manner illustrated in FIG. 7.

The heat exchanger tube is suitably mounted on the blood inlet portion 315 so that it can be interconnected to a separate source of a suitable heat exchange medium, such as water, and it is disposed in a helical coil having a size and shape adapted to fit within the chamber 318 so that it encircles the chamber axis 319. The chamber 318 defined by the housing 311 is appropriately nine to ten centimeters in diameter, and the heat exchanger tube 312 has appropriately the same diameter. Of course all, of the above dimensions are given by way of example and may be altered according to the requirements of any particular heat exchanger apparatus, all within the inventive concepts disclosed.

The illustrated heat exchanger tube 312 is fabricated from a suitable material, such as aluminum, so that it is sufficiently rigid to retain the helically configuration in which it is wound. In addition, it may be hard anodized or otherwise suitably processed for biocompatibility. It has an exterior surface 327 and a hollow interior through which to pass a heat exchange medium for purposes of exchanging heat with a quantity of blood brought into contact with the exterior surface 327.

The illustrated heat exchanger tube 312 employs what is commonly called a bellows tube configuration. It has a plurality of circumferentially-extending, spaced-apart ribs 314 that are integrally formed with the heat exchanger tube 312 to extend radially outward from the exterior surface 327. These function as spacing means disposed between the exterior surface 327 of the heat exchanger tube 312 and the scalloped inner surface 313 of the housing wall 317 for defining a flow passage through which to pass a quantity of blood so that the blood contacts a substantial portion of the exterior surface 327. In other words, they are the spacing members 314 previously mentioned. The exterior surface 327 corresponds to the small diameter section 220 of the heat exchanger tube 218 in FIG. 3, and the ribs 314 correspond to the large diameter individual ribs portion 219.

The heat exchanger tube 312 is wound in a helical coil having a plurality of windings 331-335 disposed closely together so that there is only a slight space between adjacent ones of the windings. So configured, the heat exchanger tube 312 may be described as having something like a screw configuration. Similarly, the inner surface 313 of the housing wall 320 includes a helical groove 336 that is something like an interior thread into which the heat exchanger tube 312 fits. Thus, the inner surface 313 generally faces the heat exchanger tube 312, and the two are maintained spaced apart by the spacing members or ribs 314.

This arrangement results in a generally vertical flow passage between the inner surface 313 of the housing wall 320 and the exterior surface 327 of the heat exchanger tube. It is this flow passage through which the blood passes in flowing from the blood inlet 315 to the blood outlet 316, and it does so in contact with the exterior surface 327 to provide effective heat exchange.

Referring now to FIG. 8, there is shown an enlarged cross section of a portion of the apparatus 310 taken on line 8—8 of FIG. 7 that further illustrates the abutting relationship of the heat exchanger tube 312 and the scalloped inner surface 313. Each one of the spacing members or ribs 314 generally abuts the scalloped inner surface 313 of the housing wall 320 to define a generally vertical flow passage that includes each of the passages 337 bounded by adjacent ones of the ribs 314, the exterior surface 327 and the scalloped inner surface 313.

FIG. 8 also shows the manner in which the ribs are further spaced apart toward the scalloped inner surface 313 than they are toward the chamber axis 319. This results when the heat exchanger tube is wound into the helical shape and it produces a larger flow passage.

Considering once again FIG. 7, one aspect of the invention provides inlet passage means for conveying a quantity of blood introduced into the blood inlet portion to an upper portion of the heat exchanger tube under influence of gravity. The blood inlet 315 is mounted above the chamber 318 and the blood outlet 316 below for this purpose, and the blood inlet 315 is configured to define a passage 350 that functions as means for conveying the blood to a central portion 351 of an uppermost winding 331 on the heat exchanger tube. Conveyed to this point, the blood gentle trickles down through the flow passage described above. Preferably, there is included a distribution structure 352 that extends to a lip 353 that closely conforms to the helical slant of the uppermost winding 331 for this purpose.

Referring now to FIG. 9, there is shown a cross section view of the heat exchanger apparatus 310 with a cardiotomy filter element 338 installed. The heat exchanger tube 312 is mounted within the chamber 318 to define a space 339 (FIGS. 7 and 9) encircled by the heat exchanger tube 312. This space has a size and shape sufficient to receive the filter element 338, and the blood inlet 315 may include suitable manifolding for its use.

A second heat exchanger apparatus 410 is shown in FIGS. 10 and 11. For convenience, many components are designated by reference numerals increased by one hundred over those designating similar features of the heat exchanger 310, and these will not be described further. The heat exchanger tube 412 includes an exterior surface 427, as does the heat exchanger tube 312 of the heat exchanger apparatus 310. However, the heat exchanger tube 412 does not have ribs (spacing members). Instead, a plurality of protrusions 440 are provided that are integrally attached to the housing wall 417 so that they extend radially inward toward the heat exchanger tube 412. The protrusions 440 function as spacing means in a manner similar to that of the ribs 314 of the heat exchanger apparatus 310.

At least three protrusions 440 are used for each one of the windings of the heat exchanger tube 412, and they provide spacing between the scalloped inner surface 413 and the exterior surface 427 of the heat exchanger tube 412 in an amount and manner comparable to that of the ribs 314. Of course, it is within the inventive concepts disclosed to use spacing members that are not attached to either the heat exchanger tube or the housing wall. A separate insertable member may be provided for this purpose. Using the protrusions enables use of a smooth heat exchanger tube with an exterior surface having more surface area that the blood contacts.

Thus, the blood oxygenator heat exchanger and the heat exchanger of the invention overcomes concerns of the prior art with a novel structure providing effective temperature control of blood. The heat exchanger in particular eliminates the need for the inner scalloped member 110 in FIG. 1, to provide a less costly and more conveniently fabricated structure that can also accept a filter element.

Although an exemplary embodiment of the invention has been shown and described, many changes, modifications, and substitutions may be made by one having ordinary skill in the art without necessarily departing from the spirit and scope of this invention.

What is claimed is:

1. An apparatus for changing the temperature of blood comprising:
   a housing having at least a first inner wall defining an enclosed chamber through which blood may be directed from a blood inlet portion to a blood outlet portion;
   a heat exchanger tube, formed from a tubular body having external and internal surfaces, which is wound in a helical arrangement to provide a plurality of adjacently positioned windings having a top and bottom end, said helically wound tube being dimensioned to be received in the chamber to position at least an outwardly facing portion of said external surface of each of said windings to face said at least a first inner wall, said heat exchanger tube having a plurality of individual circumferentially extending external ribs thereon and reduced cross-sectional area regions between said ribs;
   an inner member formed to fit within said coil and having a surface confronting a portion of said external surface of said tube opposite said at least a first housing inner wall;
   said at least a first inner wall having a surface facing said external surface of said windings and formed with a complimentary shape of alternating depressions and protrusions for receiving at least a portion of said heat exchanger tube;
   said at least a first housing inner wall and said inner member being placed in substantial engagement with said ribs of said heat exchanger tube while remaining spatially separated at said top and bottom ends of said heat exchanger tube to define an open pathway therebetween;
   means for directing said blood between said housing inner wall and said inner member surface over said top end of said heat exchanger tube; and
   means for directing a heat exchange fluid through said heat exchange tube.

2. An apparatus as recited in claim 1, wherein the means for directing blood over said top end of said heat exchanger tube includes:
   means for conveying the quantity of blood to a central portion of said top end of the heat exchanger tube.

3. An apparatus as recited in claim 1, wherein:
   said inner member is a separate filter element.

4. A blood heat exchanger and oxygenator comprising:
   a housing having a blood inlet, a blood outlet, an inlet for heat transfer fluid, and an outlet for heat transfer fluid, said housing including an inwardly facing circular surface which defines a substantially cylindrical chamber;
   a heat exchanger tube in said housing, said heat exchanger tube being wound into a helical coil having a plurality of windings, a generally vertical axis, with top and bottom ends and inner and outer surfaces, said coil being coupled to said inlet and said outlet for heat transfer fluid;
   said heat exchanger tube having a plurality of individual circumferentially extending external ribs thereon and reduced cross-sectional area regions between said ribs;
   an inner member fitted within said coil and having a surface confronting the inner surface of said coil;
   said inner member surface and said housing circular surface are formed with one or more depressions complimentary in shape to said wound tube, with said one or more depressions being formed to receive at least part of said tube, said housing circular surface and said inner member surface being placed into substantial engagement with said ribs of said heat exchanger tube while remaining spatially separated at said heat exchanger tube top and bottom ends to define opposing open areas to allow for the passage of a fluid over said tube outer surface;
   oxygenating means positioned and arranged within said housing for oxygenating blood; and
   wherein a portion of said oxygenating means and said open areas between said housing and inner member surface define a blood flow path extending from said blood inlet to said blood outlet.

* * * * *